United States Patent [19]
Elliott

[11] Patent Number: 6,090,400
[45] Date of Patent: Jul. 18, 2000

[54] PHARMACEUTICAL PREPARATION AND METHOD FOR TREATMENT OF DIABETES

[75] Inventor: Robert Bartlet Elliott, Auckland, New Zealand

[73] Assignee: The Trustees of the Childhood Diabetes Transplant Research Trust, Auckland, New Zealand; Robert Bartlett Elliott, Michael Anthony Helyer, Kevin Bruce Truner, Leigh Annette McGregor, David Allan Collinson, trustees

[21] Appl. No.: 08/665,357

[22] Filed: Jun. 17, 1996

Related U.S. Application Data

[63] Continuation of application No. 08/385,362, Feb. 7, 1995, abandoned, which is a continuation-in-part of application No. 08/223,945, Apr. 6, 1994, abandoned.

[30] Foreign Application Priority Data

Feb. 7, 1994 [NZ] New Zealand ............................ 250834

[51] Int. Cl.[7] ........................................................ A61F 2/00
[52] U.S. Cl. ............................................. 424/422; 514/866
[58] Field of Search ............................ 424/400, 422–426; 514/866; 435/174, 176–182, 70.1, 240.1

[56] References Cited

U.S. PATENT DOCUMENTS

| | | | |
|---|---|---|---|
| 5,262,055 | 11/1993 | Bae et al. ................................ | 210/645 |
| 5,264,220 | 11/1993 | Long ...................................... | 424/450 |

OTHER PUBLICATIONS

Sutherland D E R, Matas A J, Goetz F C, Najarian J S., Transplantation of dispersed pancreatic islet tissue in humans . . ., Diabetes 1980; 29 Suppl. 1; 31–44.

Bowen K M, Andrus L, Lafferty K, Successful allotransplantation of mouse pancreatic islets to non–immunosuppressed recipients, Diabetes 1980; 29:98.

Namikos I N, Prowse S J, Carotenuto P, Lafferty K J, Combined treatment with nicotinamide and desferrioxamine . . ., Diabetes 1986; 35:1302.

Yamada K, Nonaka K, Hanafusa T, Miyazaki A, Toyoshima H, Tarui S, Preventive and therapeutic effects of large dose. . ., Diabetes 1982; 31:749–753.

Korsgren O, Jansson L, Eizink D, Anderson A, Functional and morphological differtiation of fetal porcine isle . . ., Diabetologia vol. 34: 379–386, 1991.

Korsgren O, Groth C G, Anderson A, Hellerstron C, Tibell A, Tollemar J, Bolinder J, Ostman J, Kumagai M, Moller E, Bjoersdorff A, Transplantation or Porcine fetal pancreas to . . . Transplantation Proceedings vol. 24, No. 1; Feb., 1992: 352–353.

Sandler S, Anderson A, Long Term effects of exposure of pancreatic islets . . . Diabetologia 1986; 29–199.

Sandler S, Anderson A, Stimulation of cell replication in transplanted pancreatic islets by nicotinamide treatment; Transplantation 1988; 46(1):30–31.

Mandrup–Poulsen T, Bendtzen K, Nielsen J, Bendixen G, Nerup J, Cytokines cause functional. . ., Allergy 1985, 40:424–429 and Kolb H, Burkart U, Appels B, Hannenberg, et al, (1990), Essential contribution of macrophases to islet. . ., J Autoimmun 3:1–4.

(List continued on next page.)

Primary Examiner—Gollamudi S. Kishore
Attorney, Agent, or Firm—Jacobson, Price, Holman & Stern, PLLC

[57] ABSTRACT

A method of treatment of humans suffering from diabetes which involves transplantation into the human of viable porcine islets capable of producing insulin within its host. The invention also includes a particular preparation for such transplantation and its method of preparation which involves extraction from a piglet at near full term gestation (whether delivered prematurely or not) and treatment of the tissue within nicotinamide and/or any compound exhibiting similar growth promoting and cytoprotective effects and the subsequent administration of such a compound or compounds to the patient after the transplantation.

12 Claims, 2 Drawing Sheets

OTHER PUBLICATIONS

Yamada K, Miyajima E, Nohaka Kyohei, Inhibition o fcytokine–induced MHC class II but not class I. . ., Diabetes vol. 39: Sep. 1990: 1125–1130.

Reddy S, Bibby N, Elliott R, Dietary prevention and enhancement of diabetes . . ., Lessons from Animal Diabetes II, Third Int'l. Workshop, Mar. 1990; p. 34.

Elliott R, Reddy S, Bibby N, Kida K, Dietary prevention of diabetes in the non–obese diabetic mouse, Diabetologia 1988, 31: 62–64.

Bibby N, Elliott R B, Prevention of Diabetes in the NOD mouse with nicotinamide. . ., Abstract S. 60, Diabetes Research & Clinical Practice; vol. 14, 1991.

Korsgren O, Jansson L, Eizirik D, Anderson A, Functional morphological . . ., Diabetologia (1991) 34:379–386.

Zipris D, Labarus A, Crow A, Hadzija M, Delovitch T, Defective thymic T cell activation by concanavalin A. . ., The Journal of Immunology vol. 146: 3763–3771.

Webster's Dictionary. 1988, p. 501.

PHARMACEUTICAL PREPARATION AND METHOD FOR TREATMENT OF DIABETES

This is a Continuation of application Ser. No. 08/385,362, filed Feb. 7, 1995 which was abandoned upon the filing hereof; which in turn is a continuation-in-part of U.S. application Ser. No. 08/223,945 filed on Apr. 6, 1994, now abandoned.

The present invention relates to improvements in and/or relating to the treatment of diabetes.

The present invention relates to a method of treatment of a mammalian patient suffering from diabetes (including humans) which involves the transplantation into the mammal of viable porcine islets capable of producing insulin within its host. Such transplantation to date has not been sufficiently successful without side effects associated with concomitant continuous immunosuppression.

The present invention also comprises in preparations useful for such a method of treatment.

In a first aspect the present invention may broadly be said to comprise in a method of treating a mammalian patient suffering from diabetes which comprises transplanting into the mammal an effective amount of islets capable of producing insulin from a pig, said islets having been extracted from a piglet at near full term gestation (whether delivered prematurely or not) and which tissue has been treated during preparative procedures with nicotinamide and/or any compound exhibiting similar growth promoting and cytoprotective effects, and said patient at least for a period after such transplantation is administered (preferably orally) with nicotinamide and/or a compound exhibiting similar effects.

Preferably, the administration of nicotinamide and/or a compound exhibiting analogous effects is administered to the mammal along with a source of protein that substitutes for bovine protein including casein. Other proteins which could be substituted for bovine protein are dietary protein such as milk, fish meal, vegetable protein or human milk protein.

Preferably, said piglet from which the islets have been extracted is newborn.

Preferably, the preparation is substantially as hereinafter described and may include a cryogenic storage period prior to thawing and transplantation.

In a further aspect, the present invention comprises in a preparation capable of being injected into a mammalian patient to provide transplantation of a type referred to in the method of the present invention, said preparation having a viable insulin producing quantity of islets that have been extracted from a newborn piglet into nicotinamide and/or a compound exhibiting analogous effects.

In a further aspect, the present invention comprises in the said preparation in a cryogenically stored form.

In still a further aspect, the present invention comprises in a transplantable quantity of a preparation in accordance with the present invention having at least 100,000 porcine islets that have been and/or are in a nicotinamide containing environment and which on transplantation are able to multiply.

Upon further study of the specification and appended claims, further objectives and advantages of the invention will become apparent to those skilled in the art.

This invention has established that purified newborn piglet islets, treated with nicotinamide during the preparative procedures, can be successfully transplanted into spontaneously diabetic mice treated with nicotinamide and a cow protein free diet (Table 1).

Without the special preparation of donor tissue, and treatment of the recipient, such transplantation is unsuccessful. Such transplantation is also unsuccessful in normal mice which have been rendered diabetic by the injection of a drug (streptozotocin) which poisons the insulin producing cells.

We have successfully carried out piglet islet transplants into mice which are born without a functional immune system and have been rendered diabetic with the drug. These immunodeficient mice did not develop any infections, confirming the sterility of the islet preparations.

From these experiments, the following conclusion can be drawn:

xenotransplantation of islets (piglet to mouse) can be successfully carried out under the following conditions.
  (i) islets are purified under aseptic conditions, in the presence of nicotinamide, and can be shown to produce insulin in response to glucose, before and after cryopreservation. The amount needed for successful transplantation in mice is about 100–200,000 islet cells.
  (ii) the recipient mouse is
    (a) either spontaneously diabetic (NOD strain) or lacks a functional immune system.
    (b) receives both nicotinamide from at least the time transplantation and preferably also a cow protein free diet from at least the time of transplantation.

Variation from these conditions usually (if not always) result in failure.

Preparation of newborn piglet islets

A litter of piglets are delivered by Caesarian section and their pancreases removed under sterile surgical conditions. The pancreases are diced, and incubated with collagenase under sterile conditions. The islets are then partially purified on a density gradient, and then explanted into tissue culture containing 10 m molar nicotinamide, for 1 week. At the end of this time, further purification has occurred.

The islet cell are then checked for viability (dye inclusion) and ability to make insulin in vitro, in response to glucose. The cells and culture medium are checked for a battery of human and pig pathogens, then cryopreserved. A small batch is thawed, rechecked for viability, insulin production in vitro, sterility, and in vivo ability to reverse diabetes and in vivo sterility.

This procedure ensured that islets stored in liquid nitrogen will be viable, and sterile when thawed prior to transplantation.

A better understanding of the present invention as well as other objects, features and advantages thereof will become apparent upon consideration of the detailed description thereof, when considered in connection with the accompanying drawings wherein:

HISTORICAL REVIEW

Figure 1:
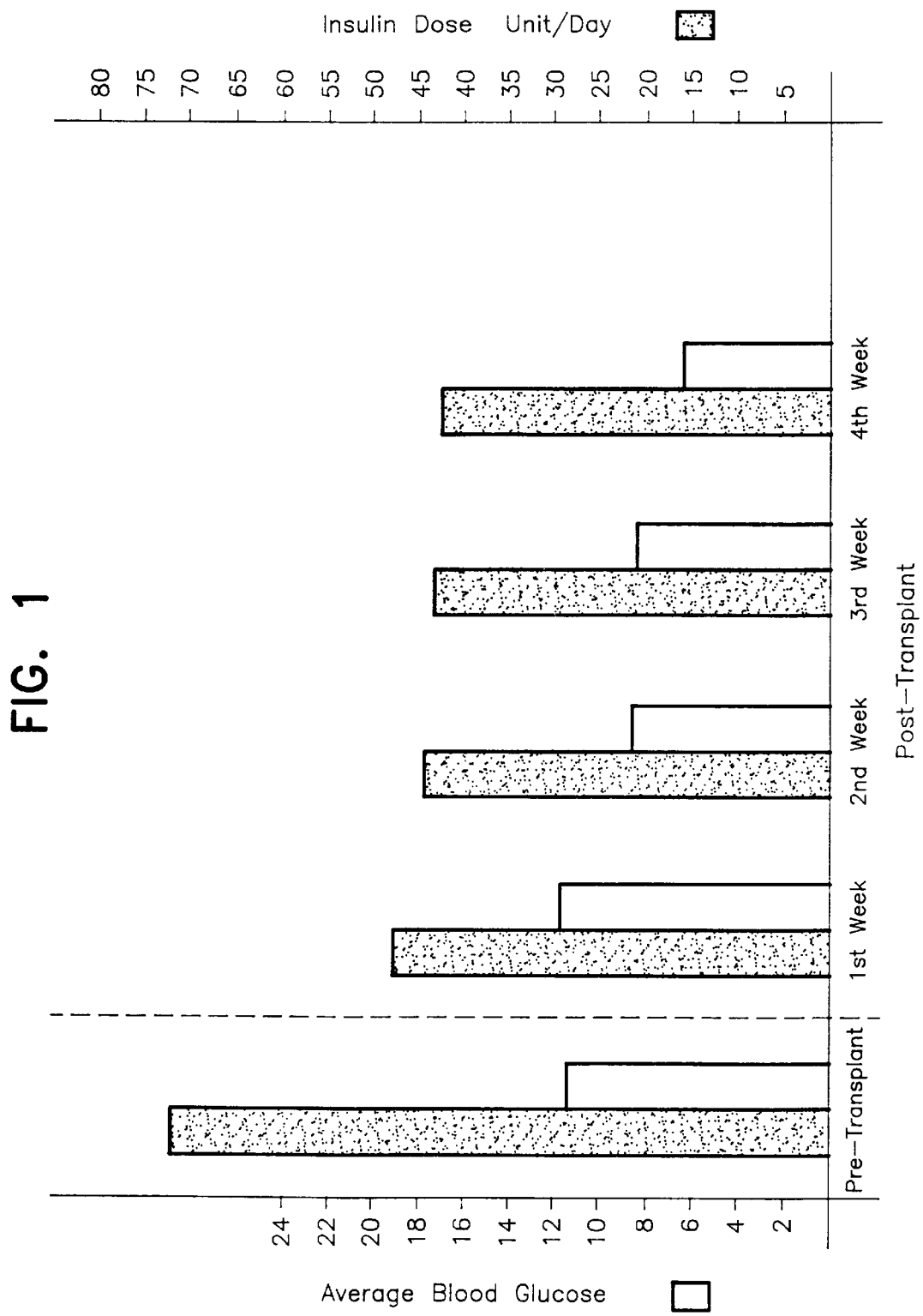
FIG. 1 is a comparison of the average blood glucose level and insulin dosage before and after transplantation of the islets.

It has been about 100 years since the first attempt to transplant viable insulin producing tissue—in this case from a dog, into diabetic humans. Islet cell allo-transplants were first attempted in the late 1970s, and efforts continue to be made up to this time. Islets from mid-trimester foetuses have been uniformly unsuccessful. Only in the 1980s did the progress of two decades of basic scientific research result in a better technique to purify a high yield of human islets.

Using closely H.L.A. matched adult donors, with great care to ensure viability, purity, and adequate numbers of islets (>200,000) some limited success has been attained in reversing diabetes (about 30% success at 1 year of follow up). In all of these attempts, the recipient has received continuous immunosuppression (which has itself presented unwanted dangers to the recipient) usually including cyclosporine. More recently, close attention to diabetes control following transplantation has been added to the protocols.

Allo-transplantation of islets into diabetic subjects has, in addition to the usual problems of vascularization and rejection common to any such transplant, the additional problem of recurrence of 'insulitis' a β cell destruction inherent to diabetes—as exemplified by the short term success, but longer term failure of pancreatic segmental transplants between identical twins discordant for diabetes. (See SUTHERLAND, D. E. R., MATAS, A. J., GOETZ, F. C., NAJARIAN, J. S., *Transplantation of dispersed islet tissue in humans; autografts an allografts*, Diabetes: 29 (Suppl. 1): 31–44) (1980).

While the ideal transplant donor tissue should be H.L.A. identical with the recipient, this is the combination most likely to result in disease recurrence in the graft.

Transplantation of mice rendered diabetic with streptozotocin with donor mouse islets different in several major H.L.A. loci has been carried out successfully, using purification technique to eliminate non-islet contaminants. (See BOWEN, K. M., ANDRUS, L., LAFFERTY, K., *Successful allotransplantation of mouse pancreatic islets to non-immunosuppressed recipients*, Diabetes, 29:98–104 (1980).

These transplants were carried out without any form of recipient immunosuppression.

However, when similar transplants were made into spontaneously diabetic (NOD) mice, they were unsuccessful, unless the recipients were treated with nicotinamide and desferrioxamine, (See NOMIKOS, I. N., PROWSE, S. J., CAROTENUTO, P., LAFFERTY,K. J., *Combined treatment with nicotinamide and desferrioxamine prevents islet allograft destruction in NOD MICE*, Diabetes, 35: 1302–1304 (1986) which appeared to prevent disease recurrence in the transplanted tissue. Nicotinamide can prevent diabetes in this strain of mouse (See YAMADA, K., NONAKA, K., HANAFUSA, T., MIYAZAKA, A., TOYOSHIMA, H., TARUI, S., *Preventative and therapeutic effects of large dose nicotinamide injections on diabetes associated with insulitis*, Diabetes 31; 749–753 (1982) although its precise mode of action is subject to much debate. Desferrioxamine is thought to act as repressor of free radical generation.

Xenotransplantation (pig to streptozotocin induced diabetic mouse) of islets has previously only been successfully carried out in athymic nude mice (See KORSGREN, O., JANSSON, L., EIZINK, D., ANDERSON, A., *Functional and morphological differentiation of fetal porcine islet like cell clusters after transplantation into nude mice*, Diabetologia, 34: 379–386 (1991).

These mice lack T cells, but are able to generate antibodies to certain antigens via nonthymic dependent B cells. While xenotransplantation may be the best option to prevent disease recurrence grafts made into spontaneously diabetic animals or humans, because of great dissimilarities in tissue antigens, the likelihood of rejection is correspondingly increased.

Pig islets have been prepared and injected into the portal vein of a diabetic human subject—with only transient evidence of production of pig (pro)insulin (See KORSGREN, O., GROTH, C. G., ANDERSON, A., HELLERSTRON, C., TIBELL, A., TOLLEMAR, J., BOLINDER, J., OSTMAN, J., KUMAGAI, M., MOLLER, E., BJOERSDORFF, A., *Transplantation or Porcine fetal pancreas to a Diabetic Patient*, Transplantation Proceedings, 24 (1): 352–353 (February 1992) xenotransplantation of other organs (spleen, liver has been notably unsuccessful despite treatment with 'state of the art' immunosuppressants (e.g., the recent Pittsburgh experiences). On the other hand, these organs cannot be rid of lymphocytes and other active antigen presenting cells.

We have succeeded with allotransplantation into diabetic NOD mice using neonatal donor tissue islets from the pig.

A novel feature has been the use of neonatal donor tissue as (i) islets are easier to prepare in partially purified form from very young animals than older animals (ii) the islets are still capable of some replication, compared with adult islets and the use of nicotinamide in the culture media used in islet preparation.

The dosage of nicotinamide for transplantation purposes is 1.2–2.4 g/m$^2$ body surface, the larger dosage being used in a few days immediately surrounding the transplantation. The preferred dosage of nicotinamide administered to the mouse recipient is a 0.5% solution of nicotinamide in water substituting for normal drinking water, given ad lib continuously for a short time before insertion of the transplant into the animal. The preferred dose of nicotinamide in humans is >150 but <300 mg/year of age/day in two or more divided doses. The maximum dose/day administered should not exceed 3 g to avoid liver toxicity. The preferred formulation of nicotinamide is preferably a slow release preparation, e.g., Enduramide®. Other compounds which have analogous activity as nicotinamide is 3-aminobenzamide. See Kallman et al., *Life Sciences*, 51:671–678 (1992).

Islets flourish in media enriched with 10 m2 nicotinamide. Cell numbers, D.N.A. content and insulin production capacity are enhanced. (See SANDLER, S., ANDERSON, A., *Long term effects of exposure of pancreatic islets to nicotinamide in vitro on DNA synthesis, metabolism and Beta cell function*, Diabetologia, 29:199 (1986).

The replication and maturation of foetal islets is improved by such treatment (See SANDLER, S., ANDERSON, A., *Stimulation of cell replication in transplanted pancreatic islets by nicotinamide treatment.* Transplantation 46 (1): 30–31 (1988).

Cytokines which induce MHC proteins also have β cell cytotoxic effects which are prevented by nicotinamide (See MANRUP-POULSEN, T., BENDTZEN, K., NIELSEN, J., BENDIXEN, G., NERUP, J., *Cytokines cause functional and structural damage to isolated islets of Langerhans.* Allerqy, 40: 424–429 (1985), and KOLB, H., BURKART, U., APPELS, B., HANNENBERG, KANTWERK-FUNK, G., KIESEL, U., FUNDA, J., SCHRAERMEYEN, U., KOLB BACHOFEN, V., *Essential contribution of macrophages to islet cell destruction in vivo and in vitro*, J. Autoimmun, 3: 1–4 (1990).

Nicotinamide pretreatment suppresses Class 2 M.H.C. expression on β cells. (See YAMADA, K., MIYAJIMA, E., NONAKA, KYOHEI., *Inhibition of cytokins-induced MHC class II but not class I. Molecule expression on mouse islet cells by Nicotinamide and 3 Aminobenzamide*, Diabetes, 39: 1125–1130 (September 1990).

Without being tied to a theory, we believe nicotinamide may therefore prevent antigen presentation by β cells during the traumatic process of purification of islets from other pancreatic components, as well as producing more and more biologically active β cells. We believe also that other compounds may exhibit a similar activity provided any such compound has functional homology with nicotinamide.

Nicotinamide alone can prevent diabetes in this strain given early enough, (See REDDY, S., BIBBY, N., ELLIOTT, R., *Dietary prevention and enhancement of diabetes in the NOD mouse, Lessons from Animal Diabetes II, Third International Workshop*, p. 34 (March 1990), as can an 'elemental' or cow protein free diet (See ELLIOTT, R., REDDY, S., BIBBY, N., KIDA, K., *Dietary prevention of diabetes in the non-obese diabetic mouse, Diabetologia*, 31: 62–64 (1988).

Neither procedure alone is sufficient to prevent disease if given near to the time when diabetes usually occurs, but given together is effective (See BIBBY, N., ELLIOTT, R. B., *Prevention of Diabetes in the NOD mouse with nicotinamide and Prosobee—Dosage and Timing are important, Abstract S. 60, Diabetes Research and Clinical Practice.*, 14 Suppl. 1. (1991).

We have found that in addition to continuance of the putative effects of nicotinamide used during the preparative procedures, an additional 'antidiabetic' effect can be obtained. This can be further enhanced by the elemental or soy protein diet.

The effects of these procedures on allotransplantation into NOD mice of BALBC islets (given I.P.) is shown in Table 1.

TABLE I

ISLET CELL ALLOTRANSPLANTS IN NON-OBESE DIABETIC MICE (NOD)

| Diabetic NOD mice | # NOD transplanted | Permanent remission # | Permanent remission % | Temporary remission # | Temporary remission % | Total No. remission # | Total No. remission % |
|---|---|---|---|---|---|---|---|
| Transplant Only | 20 | 3 | 15 | 2 | 10 | 5 | 25 |
| Transplant/ Nicotinamide | 20 | 6 | 30 | 2 | 10 | 8 | 40 |
| Nicotinamide Only | 20 | 1 | 5 | 4 | 40 | 5 | 25 |

Fisher exact Piobability Test was used and the difference between the three groups was statistically significant (0.0415).

The analysis of survival based on a proportional hazard model (PHREG) was used to assess whether or not post transplant survival was longer than expected with the general conclusion of a statistically significant benefit of transplantation compared with the survival experience of non transplanted mice (Chi square 0.0009) The survival analysis of the combined treatment compared with control group shows a statistically significant benefit of this treatment (Chi square 0.0394)

We have shown 30% permanent cure of diabetes using newborn islet cells which have been cultured for 7 days with Nicotinamide, cryopreserved and transplanted (I.P.) into NOD given nicotinamide in drinking water. Neonatal piglet islets were similarly prepared and injected into diabetic NOD mice (Table 2).

TABLE 2

PORCINE ISLET CELL ZENOTRANSPLANTS IN NON-OBESE DIABETIC (NOD) MICE

| Diabetic NOD mice | # NOD Mice transplanted | Permanent remission # | Permanent remission % | Temporary remission # | Temporary remission % | Total No. remission # | Total No. remission % |
|---|---|---|---|---|---|---|---|
| Casein free diet only | 20 | 2 | 10 | 3 | 15 | 5 | 25 |
| Nicotinamide + casein free diet | 20 | 7 | 35 | 6 | 30 | 13 | 65 |
| Nicotinamide | 16 | 1 | 6.3 | 2 | 12.5 | 13 | 18.8 |
| Transplantation Only | 13 | 2 | 15.3 | 4 | 30.8 | 6 | 46.2 |

The effect of the treatments on the diabetic status was investigated using a logistic regression model. Mice who had transplants were classified as having no remission, temporary remission or permanent remission using the number of aglycosuric days after treatment.

There was a significant difference between the treatments (p=0.0023) the nicotinamide status was found to be statistically significant (p=0.0076) 60% of the mice receiving nicotinamide and casein free diet reversed diabetes (12/20) six of them permanently, with a significant benefit from this trial compared with the other three groups.

In summary, allo, and xenotransplantation of islets into diabetic NOD mice can be successfully carried out under the conditions of the present invention.

We have successfully replicated the xenotransplantation of athymic nude mice, (See KORSGREN, O., JANSSON, L., EIZIRIK, D., and ANDERSON, A., *Functional morphological differentiation of fetal porcine islet like cell clusters after transplantation into nude mice, Diabetologia*, 34: 379–386 (1991) but have been unsuccessful with the procedure in another immunodeficient strain (severe combined immunodeficient-SCID mice). These mice lack effective T & B cells, but do have active natural killer (NK) cells.

We have also been less successful in attempts to xenotransplant Swiss mice (the non-diabetic progenitors of the NOD mouse) rendered diabetic with streptozotocin, using the same procedures which were successful in NOD (Table 3).

TABLE 3

PORCINE ISLET CELL TRANSPLANTATION INTO DIABETIC SWISS MICE (ST2)

| | # Swiss Transplanted | Permanent Remission # | Temporary Remission # | Total Remission # |
|---|---|---|---|---|
| Nicotinamide + Casein Free Diet | 9 | 1 | 3 | 4 |
| Transplant Only | 6 | 1 | 1 | 2 |

It appears that the NOD mouse behaves immunologically more like the nude mouse, than the SCID or Swiss mouse. Lazarus et al. have demonstrated 'thymic anergy' in the NOD mouse over the age of 7 weeks. (See ZIPRIS, D., LAZARUS, A., CROW, A., HADZUA, M., DELOVITCH, T., *Defective thymic T cell activation by concanavalin A and Anti CD 3 in autoimmune non-obese diabetic mice, The Journal of Immunology*, 146 (11): 3763–3771 (1991). This 'anergy' results in T-cells not being effectively 'trained' in the thymus, and thymic lymphocytes being unresponsive to Con A (Concanavalin A) and anti CD3. This defect is due to a genetically determined thymusdependent phenomenon expressed in NOD mice.

Some credence can be given to the idea that the diabetic NOD mouse may be partially immunodeficient.

Diabetes in the human is similar to the disease in the NOD mouse, and may respond to similar xenotransplantation procedures. The similarities and dissimilarities are listed below.

TABLE 4

|  | NOD MOUSE | HUMAN |
| --- | --- | --- |
| Insulin and age Dependent | + | + |
| Female > male | ++ | + |
| Insulitis, β cell destruction | +* | + |
| 'HLA' association | + | ++ |
| Associated endocrine immuno pathology | + | + |
| MHC Class 2 nonaspartate β chain 57) association | + | + |
| Islet cell antibodies | + | + |
| Insulin autoantibodies | + | + |
| Ie deficiency | + | ? |
| 'Thymic energy' | + | ? |
| Incidence | 120–300 days (post-pubertal) | 1–80 years (peripubertal predominantly) |

*initially peri-insular

The treatment of a human is as follows:

Full blood count, liver function tests, blood urea, nitrogen and creatinine will be measured. A pregnancy test will be done where relevant.

Normal insulin treatment will be continued up to 24 hours before transplantation when 4 hourly short acting insulin will be prescribed according to blood glucose tests. The last insulin injection will be given 4 hours before the transplant.

A cow's milk free diet commenced 1 week before transplantation and nicotinamide 1.2 g/m$^2$/day given as slow release preparation, (Enduramide®) in the 24 hours prior to transplantation. An additional ig of soluble nicotinamide given orally immediately prior to transplantation.

2×10$^6$ islet cells (prepared and purified in the presence of 10 mM nicotinamide) suspended in saline is then injected intraperitoneally under local anaesthetic after checking the placement of the needle intraperitoneally by x-ray with a small amount of contrast medium.

The medium of cells transplanted would, at most, contain 10–20 units of insulin, and therefore, produce a relatively mild insulin reaction, even if all were killed immediately and their insulin released. Hourly blood glucose monitoring and normal means (but without casein) following transplantation, and omission of the insulin injections due at the time transplantation is performed will minimize the effect in the unlikely even it occurs. Normal fasting adults can tolerate 10–29 units of quick acting insulin given by subcutaneous injection.

Monitoring of response
1. Insulin requirements/24 hours to maintain near euglycemia.
2. Recurrence of islet cell antibodies.
3. C-peptide measurement of 24 hour porcine urinary excretion at about monthly intervals initially used as an index of the transplant function. Further testing (oral glucose tolerance) is conducted if insulin requirement disappear.

The nicotinamide and C.M. protein free diet will be continued for at least 3 months, and probably indefinitely if insulin requirements disappear.

Uncontrolled insulin production

It is conceivable that successfully transplanted piglet islets could produce insulin even when blood glucose levels are normal. This has not happened in the piglet to mice experiments, nor in human to human (allograft) experiences internationally.

Piglets islets are killed by the drug streptozotocin, whereas human islets are not. This drug has been used in humans to control inappropriate insulin secretion from malignant islets which are sensitive to the drug. The likelihood of the above complication is exceedingly remote.

Without further elaboration, it is believed that one skilled in the art can, using preceding description to utilize the present invention to its fullest extent. The following preferred specific embodiments are therefore to be construed merely illustrative and not limitative of the remainder of the disclosure in any way whatsoever. Unless defined otherwise, all technical and scientific terms used herein have the same meaning as commonly understood by one of ordinary skill in the art to which this invention belongs. All publications mentioned are incorporated herein by reference.

CLINICAL EXAMPLES

Two such xenotransplants have been carried out in diabetic human subjects. The first was a 15 year old female who had diabetes for 7 years requiring the injection of daily dose of insulin totalling 76–78 units/day. Despite this, her diabetic blood glucose levels were poorly controlled. The Xenotransplant was carried out as above, using 200,000 islets. There was an immediate reduction in insulin requirement which reached its maximum between the 16–21st day post operatively. During this period average blood glucose control was better than preoperatively. This reduction averaged 18 less than the pretransplant dose during this period. The effect slowly waned over the next few weeks.

The second transplant involved a 15 year old diabetic male who had the disease for 7 years. On this occasion 800,000 viable islets of more than 150μ in diameter were transplanted. On this occasion, the insulin dose was reduced to a minimum of 55% of the pretransplant dose in the third week post transplant and averages 62% of the pretransplant dose in the fifth week after transplantation. The average blood glucose levels before transplantation of about 10 mm/1 have been reduced to 6.5 mm/1 in the 4th and 5th weeks. The time course of blood glucose and insulin dose in this subject are shown in FIG. 1.

It appears that the transplanted piglet islets are capable of producing insulin for at least 5 weeks after engraftment in diabetic humans and that the magnitude of the effect is related to the number of islets implanted. The duration of the effect in the second instance indicates that acute rejection of the transplanted tissue has not occurred. No side effects of the procedure have been encountered. Further transplant procedures will be carried out using a larger number of islets but in other ways not varying the technique. To date the results in humans are similar to those described in the diabetic mice transplanted with piglet islets.

Figure 2:
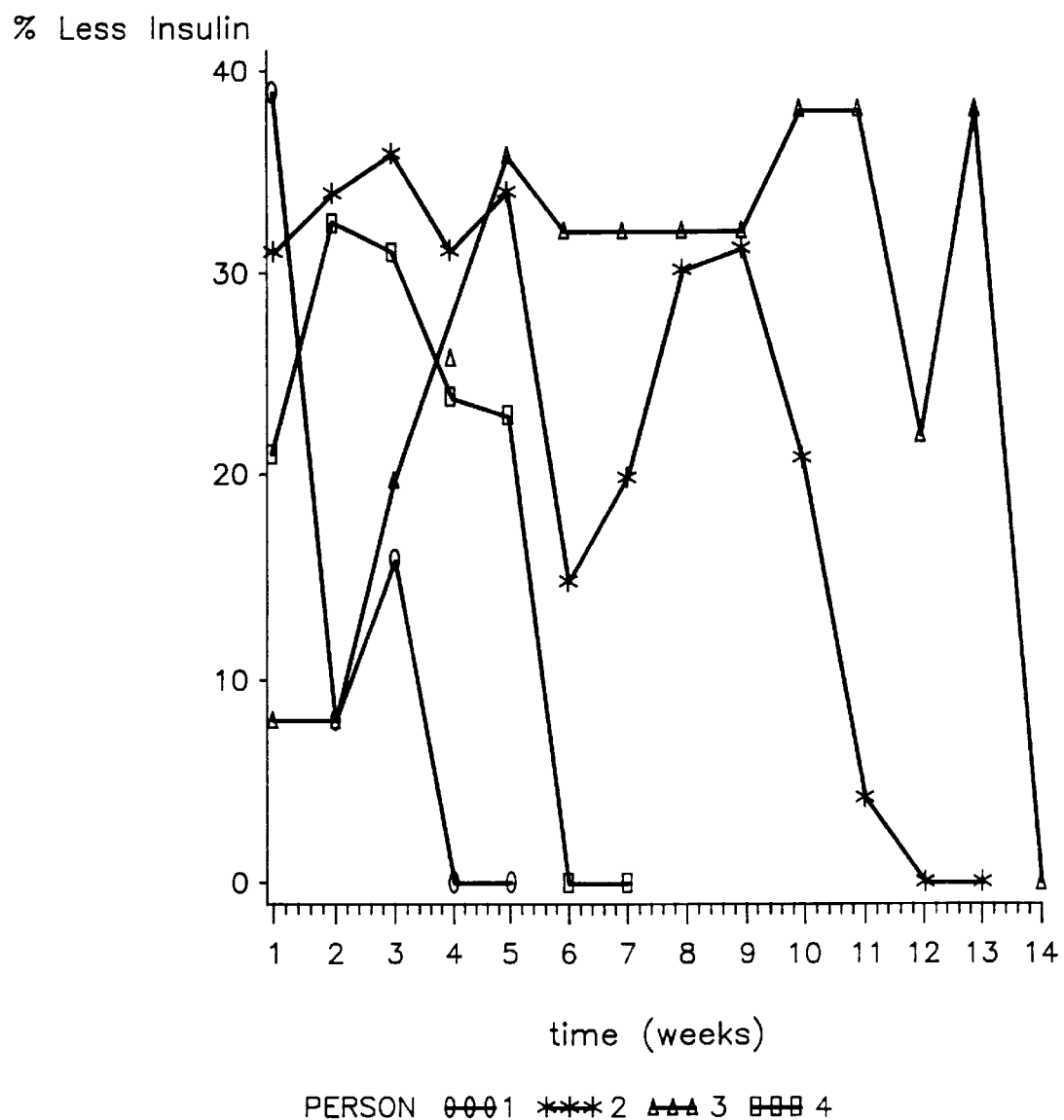
FIG. 2 shows a plot of the reduction in daily insulin dose relative to the pre-transplant level against the days after transplantation.

The reduction in daily insulin dose relative to the pretransplant level is plotted against the days after transplantation. Note FIG. 2. There is a maximum response of 40% reduction and a maximum duration of three months. Porcine C-peptide was detected in all sera taken at the time of reduction in insulin dose was greater than 10%, i.e., the reduction is likely to be the result of pig insulin secretion by the transplant. The least response was obtained with the small dose of islets.

What is claimed is:

1. A method for treatment of a mammalian patient suffering from diabetes which comprises:
   (a) extracting islet cells from piglets delivered at full term gestation;
   (b) treating said islets with nicotinamide;
   (c) injecting so as to transplant into said mammalian patient an effective amount of viable piglet islet cells which have been treated in accordance with step (b), said viable islets being capable of producing insulin in a host;
   (d) administering nicotinamide to said mammalian patient at least subsequent to transplantation; and
   (e) administering a casein-free diet to said mammalian patient.

2. The method of claim 1 wherein the mammalian patient is administered nicotinamide prior to transplantation.

3. The method of claim 1 wherein the casein-free diet is administered to the mammalian patient at least after transplantation.

4. The method of claim 1 wherein the casein-free diet is administered prior to transplantation.

5. The method of claim 1 further comprising storing the islets in a cryogenic form.

6. The method of claim 1 wherein said nicotinamide is administered to said mammalian patient orally.

7. The method of claim 1 wherein the islets have been extracted from piglets which are newborn.

8. The method of claim 1 wherein the transplantation is xenotransplantation.

9. The method of claim 1 wherein between 100,000–800,000 islets are transplanted.

10. The method of claim 1 wherein nicotinamide is administered in a dosage of between 1.2–2.4 g/m$^2$ body surface.

11. The method of claim 1 wherein said method permits transplantation without the need for immunosuppressive treatment.

12. The method of claim 1 wherein the mammalian patient is human.

* * * * *